(12) United States Patent
Fiard et al.

(10) Patent No.: US 12,090,307 B2
(45) Date of Patent: Sep. 17, 2024

(54) INJECTION DEVICE

(71) Applicant: Becton Dickinson France, Le Pont de Claix (FR)

(72) Inventors: Michael Fiard, Corenc (FR); Gilles Bernede, Arbusigny (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 17/769,859

(22) PCT Filed: Oct. 14, 2020

(86) PCT No.: PCT/EP2020/078918
§ 371 (c)(1),
(2) Date: Apr. 18, 2022

(87) PCT Pub. No.: WO2021/078605
PCT Pub. Date: Apr. 29, 2021

(65) Prior Publication Data
US 2022/0370720 A1 Nov. 24, 2022

(30) Foreign Application Priority Data
Oct. 23, 2019 (EP) .................................... 19315127

(51) Int. Cl.
*A61M 5/315* (2006.01)
*A61M 5/31* (2006.01)
*A61M 5/32* (2006.01)

(52) U.S. Cl.
CPC ........ *A61M 5/3158* (2013.01); *A61M 5/3129* (2013.01); *A61M 5/3234* (2013.01)

(58) Field of Classification Search
CPC ........ A61M 2005/3267; A61M 5/3271; A61M 2005/3265; A61M 2005/3264; A61M 5/3243; A61M 5/3272; A61M 5/3202; A61M 5/3257; A61M 5/326; A61M 2005/3246; A61M 37/0015; A61M 2037/0023; A61M 2037/0061; A61M 5/3204; A61M 5/3205; A61M 2005/3254
See application file for complete search history.

(56) References Cited

U.S. PATENT DOCUMENTS 11,260,181 B2 3/2022 Kemp
2004/0225262 A1* 11/2004 Fathallah ............... A61M 5/326
604/110

(Continued)

FOREIGN PATENT DOCUMENTS

EP 3019216 A1 7/2013
WO 2015004049 1/2015

*Primary Examiner* — Dung T Ulsh
(74) *Attorney, Agent, or Firm* — The Webb Law Firm

(57) ABSTRACT

An injection device for injecting a substance into a body, including a syringe having: a needle, a barrel, a stopper, a plunger rod, moveable from an initial position to a final position, a needle shield, moveable at least from a retracted position to a safety position, a locking unit, arranged to lock the needle shield into the safety position, a locking actuator moveable at least: from a non-actuating position, into which the locking unit is in an open mode, to an actuating position, into which the locking actuator is arranged to put the locking unit in closed mode so that the needle shield can be locked into the safety position.

15 Claims, 9 Drawing Sheets

(56) References Cited

U.S. PATENT DOCUMENTS

| | | | |
|---|---|---|---|
| 2006/0189933 A1* | 8/2006 | Alheidt | A61M 5/326 604/110 |
| 2009/0270804 A1* | 10/2009 | Mesa | A61M 5/24 604/111 |
| 2011/0092915 A1* | 4/2011 | Olson | A61M 5/3243 604/198 |
| 2011/0319833 A1* | 12/2011 | Chun | A61M 5/326 604/198 |
| 2016/0199588 A1 | 7/2016 | Kemp | |
| 2016/0375195 A1 | 12/2016 | Fabien | |
| 2019/0314577 A1 | 10/2019 | Hirschel et al. | |
| 2020/0397999 A1* | 12/2020 | Franke | A61M 5/3204 |

\* cited by examiner

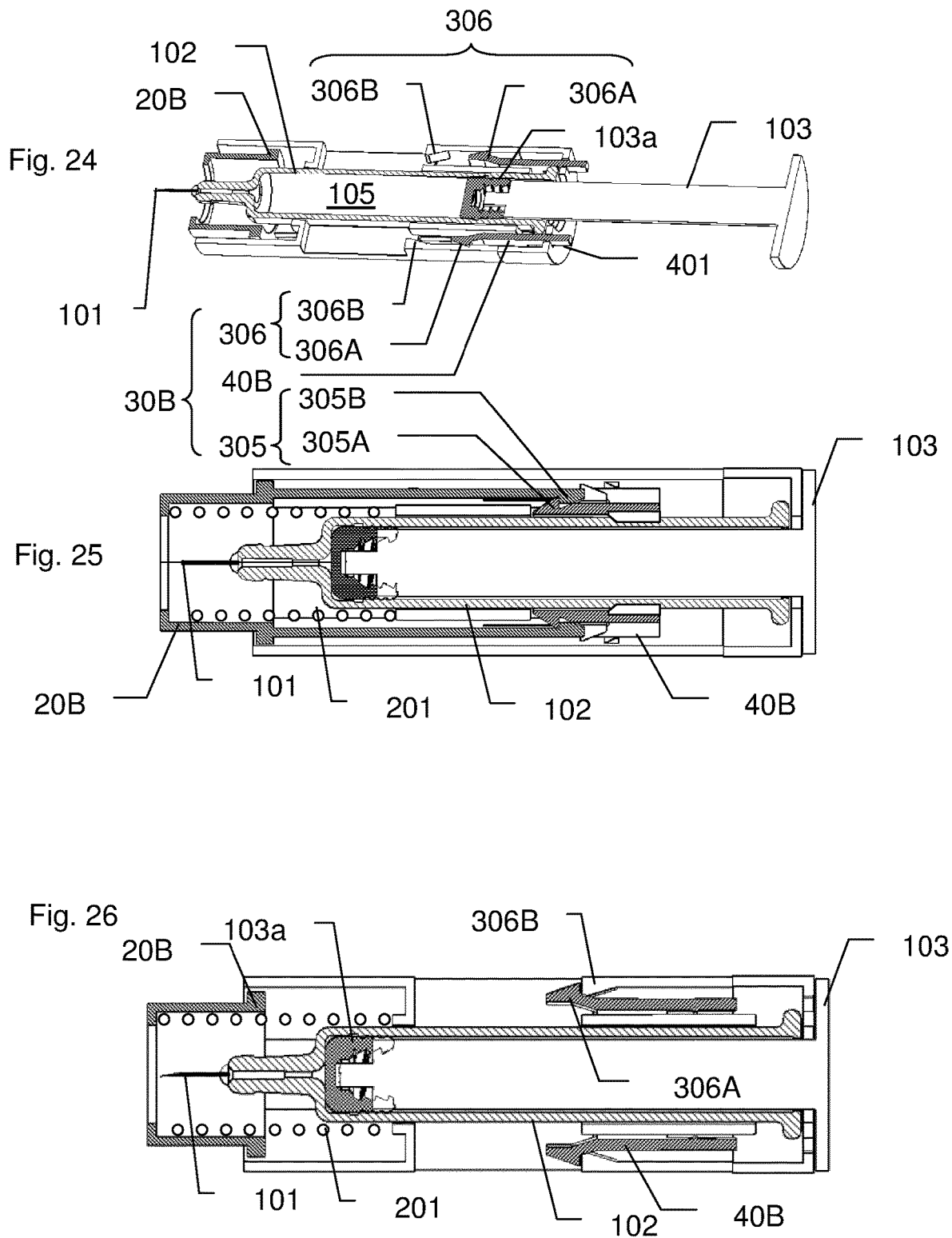

INJECTION DEVICE

CROSS-REFERENCE TO RELATED APPLICATIONS

This application is the United States national phase of International Application No. PCT/EP2020/078918 filed Oct. 14, 2020, and claims priority to European Patent Application No. 19315127.1 filed Oct. 23, 2019, the disclosures of which are hereby incorporated by reference in their entirety.

BACKGROUND OF THE DISCLOSURE

The present invention relates to an injection device, and in particular, the invention relates to a medical injection device to be used by a user to inject a substance into a body and comprising a needle shield arranged to cover the needle when the injection device is not used, to avoid unexpected injury of users.

DESCRIPTION OF RELATED ART

Injection devices with needle shields are known. Such needle shields are typically in a deployed position before use of the injection device to avoid unexpected injury, and move to retracted position during regular pricking/injection, and then move back to the initial position where there are locked after use, to allow safe manipulation/discarding without unexpected injuries.

However, the locking in the initial position of the needle shield after movement from the retracted position back to the initial position might be problematic. Indeed, in case the user needs to change of pricking site, such locking will prevent a further movement from the initial position to the retracted position, thereby preventing any change of site/further or multiple pricking thus leading to discard the injection device still containing the substance to inject.

Document EP3019216A1 discloses an auto-injector. Document US2019314577A1 discloses an automatic injection device for administering a fixed dose. Document US2016375195A1 discloses an auto-injector.

SUMMARY OF THE DISCLOSURE

The present invention aims to address the above mentioned drawbacks of the prior art, and to propose first an injection device comprising a needle and a needle shield covering the needle to avoid fear of needle before use and avoid injuries after use, the needle shield being locked after use of the injection device, while the user can inject the substance to inject in several rows. In other words, the invention aims to propose an injection device comprising a needle and a needle shield lockable in a safety position after use, while the user can inject a first portion of the substance to inject, change of pricking site and inject the rest of the substance to inject.

In this aim, a first aspect of the invention is an injection device for injecting a substance into a body, comprising:
  a syringe comprising:
    a needle to prick the body,
    a barrel arranged to contain a dose of the substance to be injected,
    a stopper a arranged in sliding engagement inside the barrel,
  a plunger rod coupled to the stopper, moveable from an initial position to a final position and to be actuated by a user to inject the dose of the substance,
  a needle shield, arranged to be moveable at least from a retracted position in which the needle can prick the user during injection, to a safety position in which the needle shield covers the needle after injection,
  a locking unit, arranged to lock the needle shield into the safety position after injection, characterized:
in that the locking unit comprises a locking actuator, the locking actuator being moveable at least:
    from a non-actuating position, into which the locking unit is in an open mode so that the needle shield can freely move between the retracted position and at least an intermediate position arranged or located between the retracted position and the safety position,
    to an actuating position, into which the locking actuator is arranged to put the locking unit in a closed mode so that the needle shield can be locked into the safety position,
and in that the locking actuator is moved by the plunger rod from the non-actuating position to the actuating position when the plunger rod reaches a threshold position.

According to the above embodiment, the injection device comprises an intermediate part, a locking actuator, to be moved by the plunger rod, and having at least two positions, each position defining a specific operation of the needle shield. In a first position (non-actuating position) of the locking actuator, the needle shield can move from the safety position or the intermediate position to the retracted position and vice versa several times, allowing the user to change of pricking site (the locking unit is in the open mode). In a second position (actuating position) of the locking actuator, the needle shield, arriving in the safety position, can be locked into the safety position, so that any further movement of needle shield will be impossible (the locking unit is in the closed mode: the needle shield arriving in the safety position will be locked in that position). In other words, the locking actuator, an intermediate part, is distinct from the plunger rod and from the needle shield. The locking actuator is arranged to be released from its non-actuating position by the plunger rod arriving in the threshold position. Once released from its non-actuating position, the locking actuator can move to the actuating position in which it can interact with the locking unit so as to activate the latter for locking the needle shield.

It has to be kept in mind that the needle shield of the injection device according above embodiment might typically present an initial shielding position (before pricking) in which it covers at least partially the needle. In other words, the needle shields typically moves from the initial shielding position to the retracted position while inserting the needle, and moves from the retracted position to the safety position while removing the needle.

In detail, the locking actuator is arranged to cooperate with the locking unit so as to close or activate the latter only when the plunger rod arrives in the threshold position (typically the threshold position is close to or equal to the final position). In the first position (non-actuating position) of the locking actuator, the locking unit is an open mode, that is to say not in a state into which it can lock the needle shield. In other words, the needle shield can freely move backward and forward. In the second position (actuating position) of the locking actuator, the locking unit is in a closed mode (actuated by the locking actuator), so that it is in a state into which it can lock the needle shield when it arrives in the safety position.

The locking unit in the present disclosure might typically comprise one or several parts or components, and/or might also comprise one or several portions of different components which cooperate together to lock the needle shield.

In summary, the locking actuator is an intermediate part arranged to be pushed or moved by the plunger rod, and arranged to cooperate with or to actuate the rest of the locking unit so that the needle shield can be locked by the locking unit only when the plunger rod has reached the threshold position.

In particular, once the locking actuator has reached the actuating position, the needle shield is in the retracted position, as at that moment, the user is ending the injection. Then the locking unit (put in the closed mode by the locking actuator) is ready to lock the needle shield, but the needle shield still has to move from the actual retracted position to the safety position. In other words, when the locking actuator reaches the actuating position, it puts the locking unit in the closed mode, and the needle shield has to move a last time to the safety position where it will be locked by the (actuated) locking unit in the closed mode.

Advantageously, the intermediate position is an initial shielding position into which the needle shield covers at least at tip or a part of the needle before use of the injection device. In other words, in the intermediate position, the needle shield prevents fear of the needle.

In a first alternative, the initial shielding position and the safety position are same positions.

In a second alternative, the initial shielding position and the safety position are different positions. In particular, the needle shield in the safety position can deploy out of the injection device more than in the initial shielding position.

Advantageously, the locking actuator is moveable from the non-actuating to the actuating position according to a linear movement along an axial direction of the injection device, and/or the plunger rod. In particular, the locking actuator is pushed by the plunger rod to move in the same direction of movement as the plunger rod. The locking actuator is translated from the non-actuating to the actuating position by the plunger rod.

According to a first embodiment, the locking unit comprises a track, and a protrusion arranged to slide in the track, and:
  the track is provided on or joined to one of the locking actuator and the needle shield, the protrusion is provided on or joined to the other of the locking actuator and the needle shield,
  the track comprises a first track portion, and a second track portion,
  the locking actuator is arranged to push the protrusion from the first track portion to the second track portion when the locking actuator moves from the non-actuating position to the actuating position.

In the above embodiment, the locking unit comprises two track portions, each track portions being designed to allow specific relative movements between the needle shield and the barrel or an external case of the injection device: the protrusion in the first track can have free back and forward movements, and in contrast, the protrusion in the second track cannot move back when the needle shield arrives in the safety position.

Advantageously, the second track comprises a recess or a locking portion arranged to receive and to block the protrusion, and to prevent a back movement of the protrusion when the needle shield is in the safety position.

Advantageously:
  the first track portion has a first length so that the needle shield can freely move along a first stroke between the initial shielding position to the retracted position,
  the second track portion has a second length. The second length may be greater than the first length, so that the safety position is separated from the intermediate position or initial shielding position by an additional stroke of the needle shield out of the device.

According to the above embodiment, the needle shield has to move by an extra stroke to move from the initial shielding position to the safety position. In other words, before injection, the needle shield in the initial shielding position covers the needle, and after injection, in the safety position the needle shield has further moved out of the injection device, to cover more the needle, to provide extra safety or other function, so as to provide a different aspect to inform that the device has already been used.

Advantageously, the locking unit comprises a flexible leg having a free end arranged between the first track portion and the second track portion, and the flexible leg is flexed by the protrusion passing from the first track portion to the second track portion. Therefore, the flexible leg automatically flexes back to its rest position, closing the way back to the first track portion.

Advantageously, the free end of the flexible leg is a backstop preventing the protrusion to go back to the first track portion, after the protrusion has been pushed into the second track portion.

According to the above embodiment, the flexible leg is an anti-backward movement: once into the second track portion, the protrusion cannot move back into the first track portion.

Advantageously, the locking actuator comprises a flexible tab arranged to deploy only when the locking actuator is in the actuating position, so as to lock the locking actuator into the actuating position. As an example, the flexible tab can deploy to abut against a wall of an external case of the injection device. Any movement of the locking actuator back to the non-actuating position is impossible.

Alternatively, according to a second embodiment:
  the locking unit comprises a first coupling unit arranged to couple the needle shield with the locking actuator only when the locking actuator is in the actuating position,
  the locking actuator coupled with the needle shield is moveable from the actuating position to a locking position,
  the locking unit comprises a second coupling unit arranged to lock the locking actuator in the locking position.

According to the above embodiment, the locking actuator, moved into the actuating position by the plunger rod, can couple with the needle shield via the first coupling unit, and it is the locking actuator, moved to the locking position, which couples or engages the second coupling unit to be locked. It has to be noted that the second coupling unit couples the locking actuator with a part linked to the barrel so as to lock the needle shield into the safety position via the whole device. In this embodiment, in addition to actuate the locking unit into the closed mode, the locking actuator participates to lock the needle shield into the safety position.

Advantageously, the first coupling unit and/or the second coupling unit is a snap fit unit comprising:
a male portion,
a female portion,
an elastic portion arranged to deflect during coupling to allow engagement of the male portion with the female portion, and to maintain after coupling engagement of the male portion with the female portion.

Advantageously, the Injection device comprises a first mechanical stop defining an initial shielding position, so that the needle shield can freely move along a free stroke between the initial shielding position to the retracted position, wherein when the needle shield is coupled with the locking actuator, the first coupling unit allow the needle shield to pass over the first mechanical stop, so that the safety position is separated from the initial shielding position by an additional stroke of the needle shield.

According to the above embodiment, the needle shield has to move by an extra stroke to move from the initial shielding position to the safety position. In other words, before injection, the needle shield in the initial shielding position covers the needle, and after injection, in the safety position the needle shield covers more the needle, to provide extra safety or other function, so as to provide a different aspect to inform that the device has already been used.

Advantageously, the injection device comprises elastic means, such as an elastic component, such as a spring, arranged to push the needle shield into the safety position.

In the above embodiment, the injection device comprises a spring which automatically pushes the needle shield to the safety position. The same spring also participates to automatically secure the locking, by urging the locking unit in a final state into which parts are mechanically engaged so as to prevent any backward movement of the needle shield.

Advantageously, the Injection device comprises:
an end of injection indicator embarked on the locking actuator,
a window, arranged:
to hide from a user the end of injection indicator when the locking actuator is in the non-actuating position,
to render visible to the user the end of injection indicator when the locking actuator is in the actuating position.

According to the above embodiment, the locking actuator, as being moved by the plunger rod, also provides the function to inform the user that the dose has been completely injected.

Advantageously, the Injection device comprises:
a safety indicator embarked on the needle shield,
a skirt, arranged:
to hide from a user the safety indicator when the needle shield is not in the safety position,
to render visible to the user the safety indicator when the needle shield is in the safety position.

According to the above embodiment, the needle shield reaching the safety position is used to inform the user that the injection device has already been used.

Advantageously, the threshold position is located in a range of 70%-100% of the stroke of the plunger rod from the initial position to the final position, preferably in a range of 85%-100% of the stroke of the plunger rod, and more preferably in a range of 95%-100% of the stroke of the plunger rod.

In the above embodiment, the threshold position is reached when the plunger rod arrives in its final position, at a moment when change of site is not needed anymore, so that the locking unit can be activated by the locking actuator.

Advantageously, the locking actuator comprises a projection, arranged to protrude out of an external surface of the injection device, arranged to be pushed by the plunger rod when the plunger rod moves the locking actuator from the non-actuating position to the actuating position. The projection can have a dimension of few millimetres, 1 mm, or 2 mm for example.

Advantageously, the Injection device comprises a needle cap, to be detached from the injection device by the user before use.

Advantageously, the Injection device comprises the dose of the substance to be injected.

Advantageously, the plunger rod is arranged to move from the initial position to the final position exclusively by application of a manual effort of the user. In other words, the injection device is not an automatic injection device.

It should be noted that all the above features can be combined or dissociated provided there is no technical contradiction.

BRIEF DESCRIPTION OF THE DRAWINGS

Other features and advantages of the present invention will appear more clearly from the following detailed description of particular non-limitative examples of the invention, illustrated by the appended drawings where:

FIG. 24 represents a perspective view of another cross section of the injection device of the second embodiment during injection;

FIG. 25 represents a cross section of the injection device of the second embodiment after injection;

FIG. 26 represents another cross section of the injection device of the second embodiment after injection.

DETAILED DESCRIPTION

Figure 1:
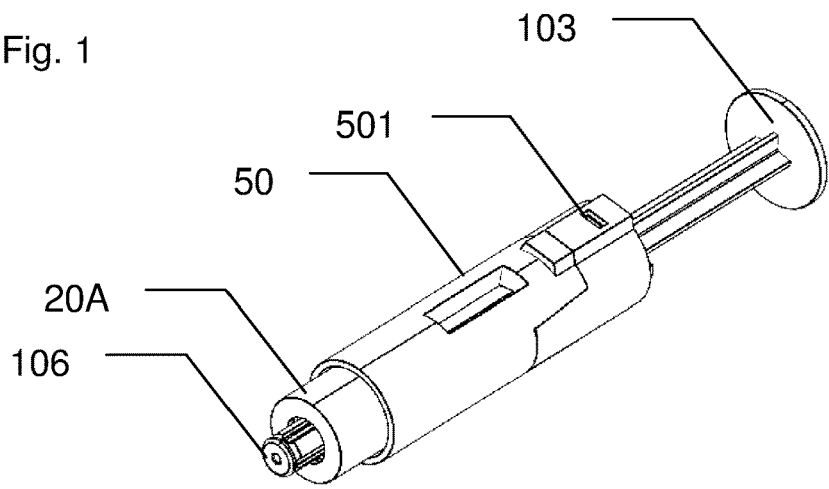
FIG. 1 represents a front perspective view of an injection device according to a first embodiment of the invention, before use.
Figure 2:
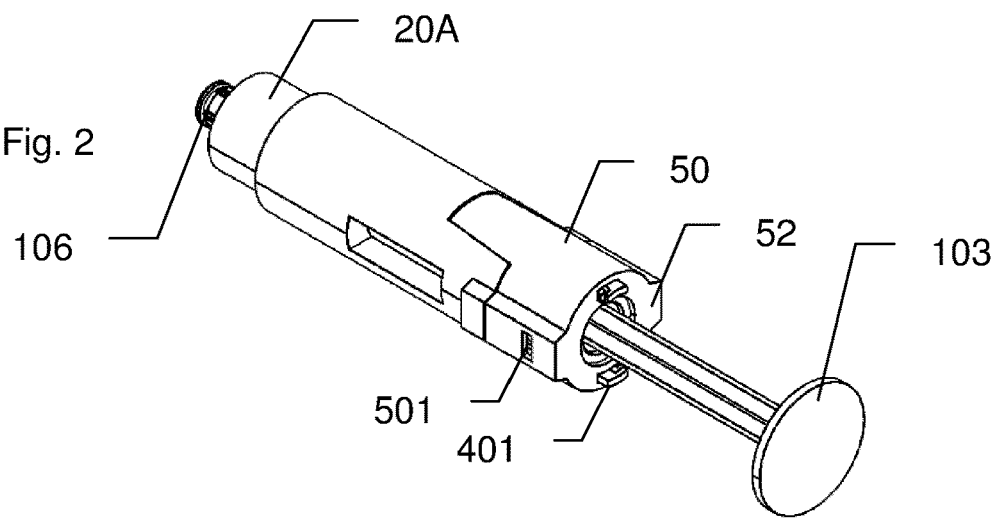
FIG. 2 represents a rear perspective view of the injection device of FIG. 1.

FIGS. 1 and 2 represent perspective views of an injection device according to a first embodiment before use, and comprising an external case 50 made of two shells, a needle shield 20A, a protective cap 106, and a plunger rod 103 visible on these figures.

Figure 14:
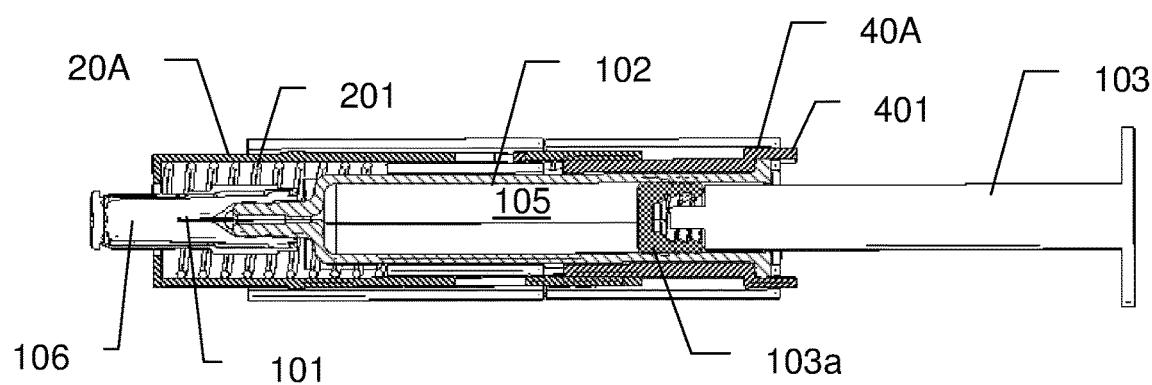
FIG. 14 represents a cross section of the injection device of the first embodiment before use.

In detail, and switching to FIG. 14 to list the main components of the injection device of the first embodiment, the injection device comprises inside the external case 50:
   a syringe comprising:
      a needle 101 to prick the body,
      a barrel 102 containing a dose of the substance 105 to be injected, and coupled to the external case 50
      a stopper 103a arranged in sliding engagement inside the barrel 102,
      a plunger rod 103 coupled to the stopper 103a, moveable from an initial position (as shown FIG. 1-4) to a final position (shown FIGS. 5-6) and to be actuated by a user to inject the dose of the substance 105,
   a needle shield 20A, in an initial shielding position in which the needle shield 20A covers the needle 101 (as shown FIGS. 1-4 and 14),
   a locking actuator 40A
   a spring 201, pushing the needle shield 20A to the left side of FIG. 14, to maintain it into the initial shielding position.

Reverting back to FIGS. 1 and 2, the injection device is here in a state before use, as the protective cap 106 is fully covering the needle to prevent contamination and/or unexpected pricking. For example, the protective cap is attached to the syringe (or to the needle shield 20A or to the external case 50) via a snap fit engagement, or via frangible portions to be torn by the user to remove the protective cap 106.

Figure 3:
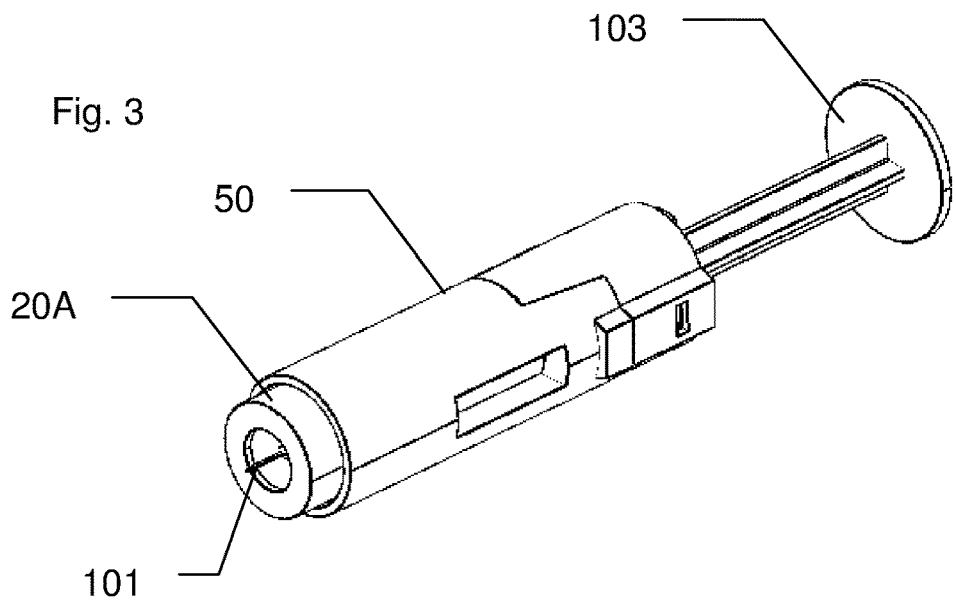
FIG. 3 represents a front perspective view of the injection device of FIG. 1, after a protection cap has been removed.
Figure 4:
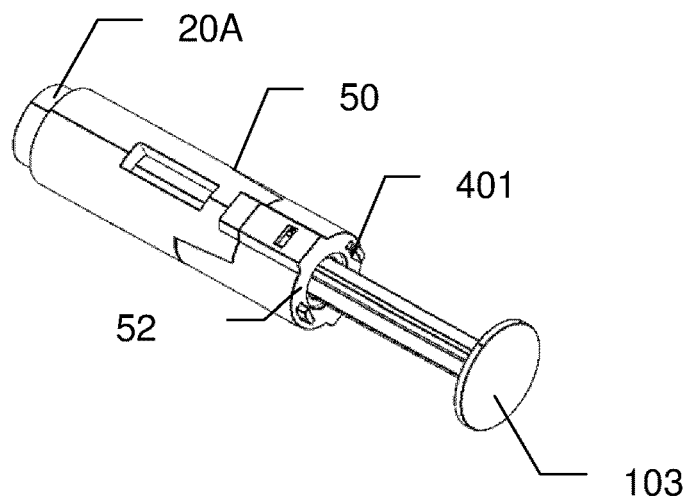
FIG. 4 represents a rear perspective view the injection device of FIG. 3.

FIGS. 3 and 4 represent the injection device at the beginning of a pricking phase, as the protective cap 106 has been removed, and the needle 101 is protruding a bit out of the needle shield 20A, being visible on FIG. 3. Indeed, in the represented state of FIG. 3, the needle shield 20A is not anymore in the initial shielding position, as it has been moved a bit into the external case 50 compared to FIG. 1. Consequently, pricking a user has started and user can finish to prick and/or can start to push the plunger rod 103 to inject the substance 105.

Figure 5:
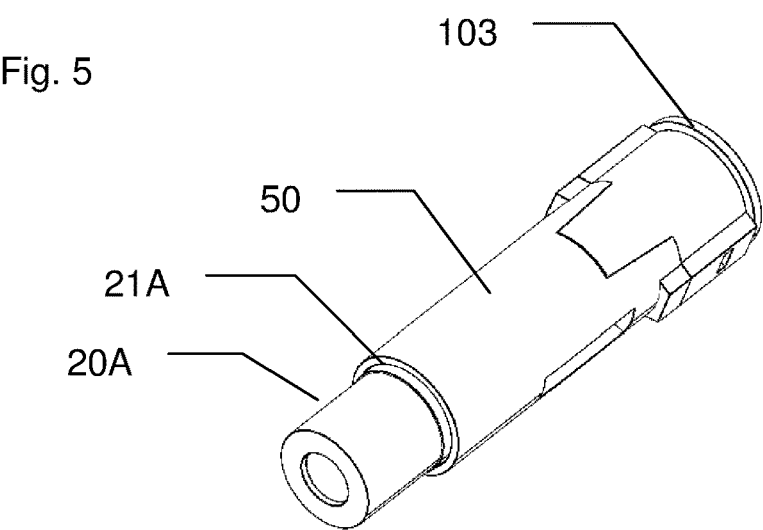
FIG. 5 a front perspective view of the injection device of FIG. 1, after use.
Figure 6:
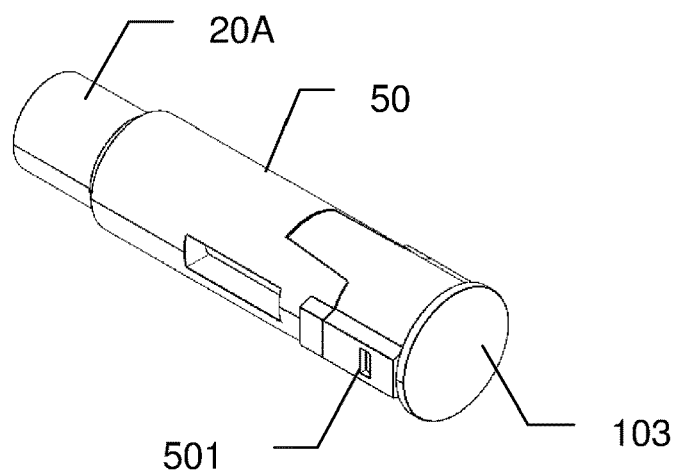
FIG. 6 represents a rear perspective view the injection device of FIG. 5.

FIGS. 5 and 6 represent perspective views of the injection device after injection, as the plunger rod 103 has been fully pushed into the barrel 102, and has arrived in its final position. One should note that the needle shield 20A is fully deployed from the external case 50, as it has reached a safety position. In this safety position, the needle shield 20A fully covers the needle 101. Also, a window 501 is shown FIGS. 1 and 6, and the function associated to this window 501 will be explained later.

A first aspect of the invention is to provide the capacity to change of pricking site even after a portion of the substance 105 has been injected (requiring the possibility for the needle shield 20A to move forward and backward), and to still ensure that after full injection, the needle shield 20A will be secured or locked into the safety position, to avoid unexpected injury or pricking.

Figure 7:
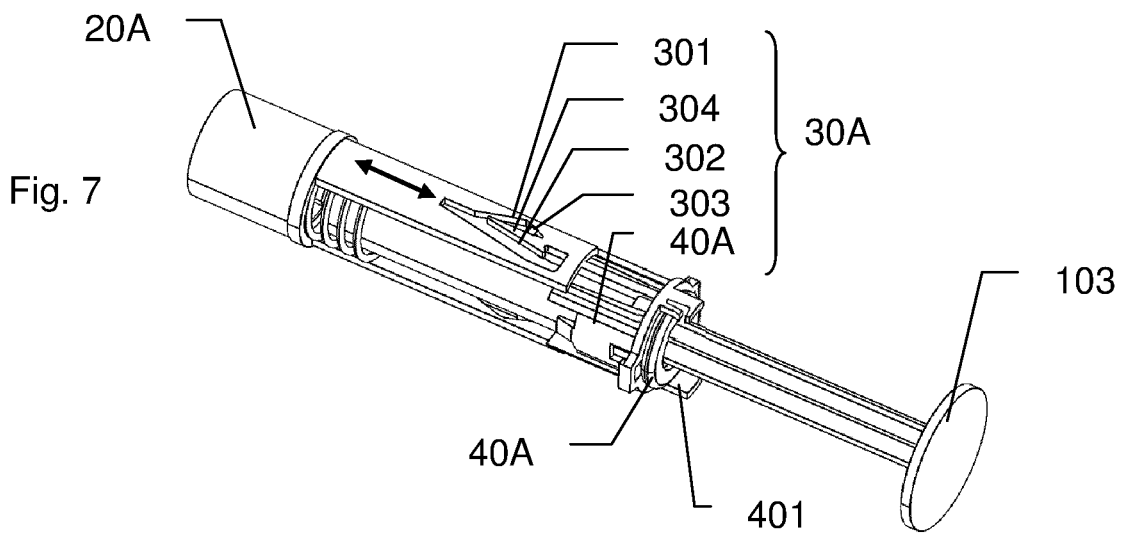
FIG. 7 represents the injection device of FIG. 4, with an external case not shown.
Figure 13:
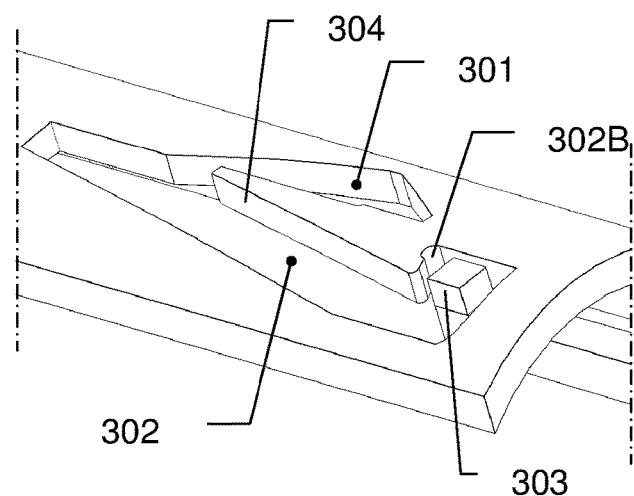
FIG. 13 represents a detail of a locking unit of the injection device of the first embodiment.

In this aim, the injection device comprises a locking unit 30A, visible FIG. 7 where the external case 50 is not shown. The locking unit 30A mainly comprises the locking actuator 40A, a track provided on the needle shield 20A, with a first track portion 301 and a second track portion 302, separated by a flexible leg 304. The locking unit 30A also comprises a protrusion 303 provided on the locking actuator 40A. FIG. 13 shows in detail the first track portion 301, second track portion 302 and protrusion 303 (located in this figure in second track portion 302). It should be noted that the track could be provided onto the locking actuator 40A and the protrusion could be provided onto the needle shield 20A.

Figure 12:
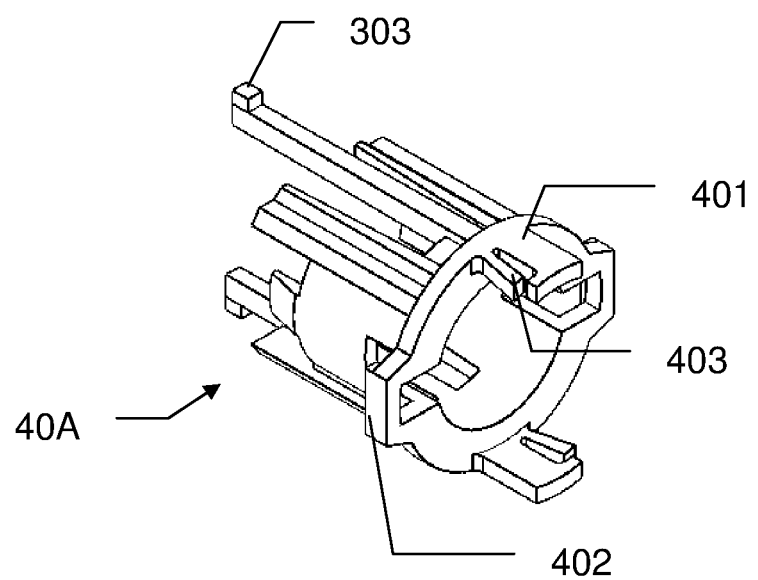
FIG. 12 represents a locking actuator of the injection device of the first embodiment.

As shown FIG. 12, the locking actuator 40A also comprises a projection 401, which is protruding out of the external case 50, as visible FIGS. 2 and 4, until the plunger rod 103 has not reached its final position. On FIGS. 2, 4, 7, the locking actuator 40A is in a non-actuating position.

Figure 8:
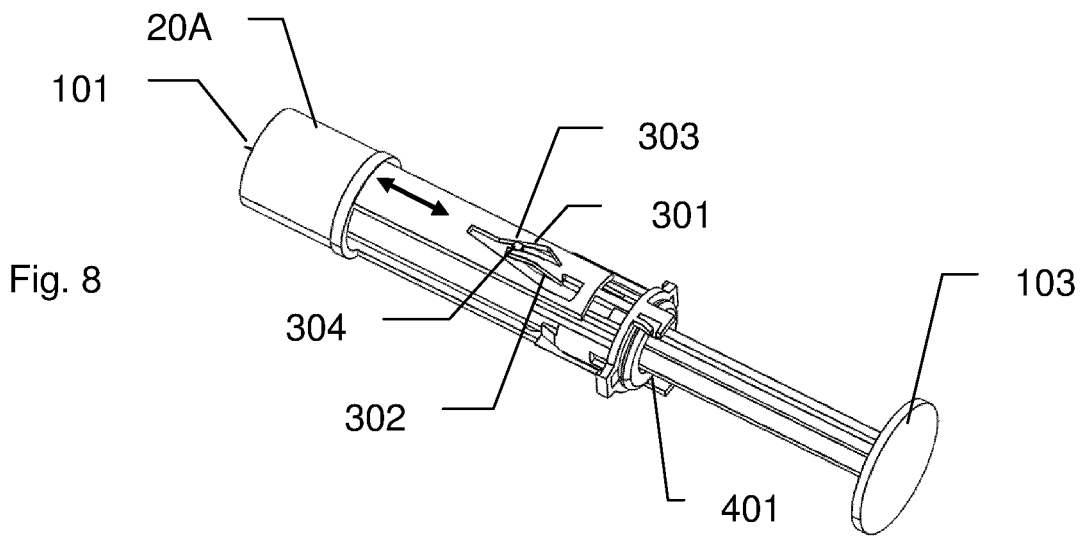
FIG. 8 represents the injection device of FIG. 7, during injection.

Consequently, the locking unit 30A is in an open mode: the protrusion 303 can freely slide in the first track portion 301, in both directions of the first track portion. This allows the needle shield 20A to move freely from the initial shielding position to the retracted position and vice versa, as shown FIG. 7 and FIG. 8. This allows a change of pricking site, the needle shield 20A being free to move from initial shielding position to the retracted position.

In a next phase, at the end of injecting the substance 105, the plunger rod 103, when approaching the final position, will contact the projection 401, and will push the locking actuator 40A from the non-actuating position to the actuating position. As shown FIG. 8, the needle shield 20A is in retracted position, and the plunger rod 103 has started to push to the left of the figure the locking actuator 40A, thereby pushing the protrusion 303 out of the first track portion 301, to the second track portion 302.

Figure 9:
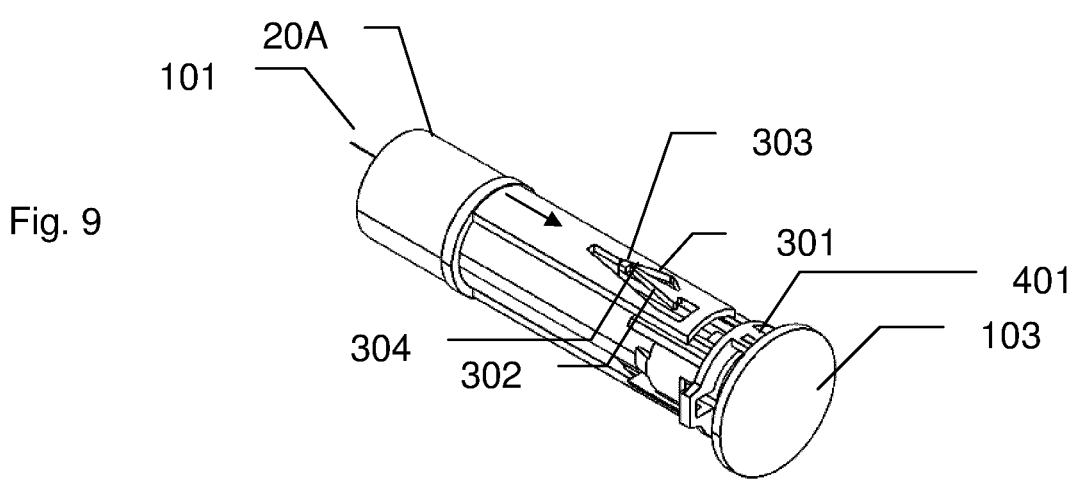
FIG. 9 represents the injection device of FIG. 7, in a final phase of injection.
Figure 10:
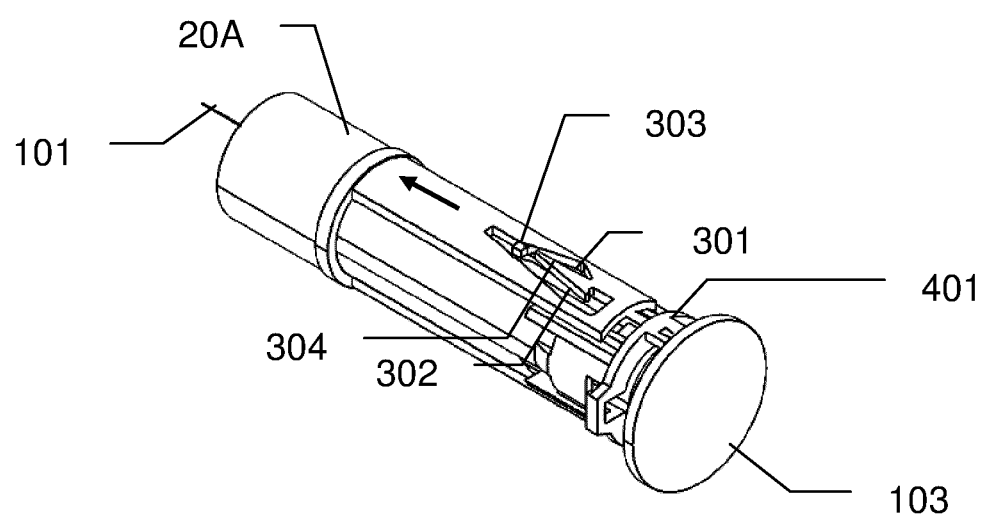
FIG. 10 represents the injection device of FIG. 9, in a further final phase of injection.

One should note that the flexible leg 304 has been flexed by the protrusion 303 (visible FIG. 8), and has come back into its non-flexed position (visible FIG. 9). Consequently, the protrusion 303 cannot move back to the first track portion 301. Finally, the plunger rod 103 finishes to push the locking actuator 40A on FIG. 10, and the protrusion 303 has completely moved to the second track portion 302. The locking unit 30A is in a closed mode: the needle shield 20A can be locked in the safety position.

Figure 11:
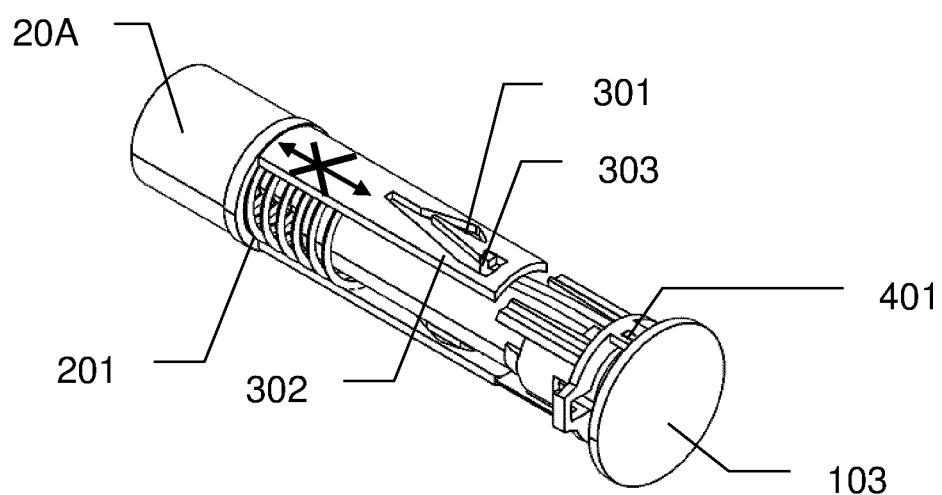
FIG. 11 represents the injection device of FIG. 9, after injection.

FIG. 11 shows the injection device after the user has removed its needle 101 out of the body, thereby allowing the needle shield 20A to move to the safety position (pushed by the spring 201 visible FIGS. 14-16), and the protrusion 303 has slid along the second track portion 302 to reach a recess 302B visible FIG. 13, into which it cannot move anymore relatively to the needle shied 20A. Consequently, the needle shied 20A is locked into the safety position.

To secure this locking, and as shown FIG. 12, the projections 401 of the locking actuator 40A are provided with flexible tabs 403 arranged to be flexed by external case 50 until the locking actuator 40A is not in the actuating position, and to deploy under a wall 52 (shown FIGS. 2 and 4) of the external case 50 when the locking actuator 40A arrives in the actuating position. Accordingly, the deployed flexible tabs 403 abut on the internal face of wall 52 of the external case 50 and prevent any backward movement of the locking actuator 40A versus the rest of the injection device, and by way of consequence, provide fully securing and locking of the needle shield 20A into the safety position.

Between FIGS. 7-8 and FIGS. 10-11, the locking actuator 40A has moved from the non-actuating position to the actuating position. As visible FIG. 12, the locking actuator 40A comprises a radial protrusion 402, arranged to cooperate with the window 501 visible FIGS. 1, 2, 6. In the non-actuating position of the locking actuator 40A, the radial protrusion 402 is not in regards of the window 501, and a user cannot see the radial protrusion 402. In contrast, in the actuating position of the locking actuator 40A, the radial protrusion 402 is in regards of the window 501, and a user can see the radial protrusion 402. This can be used to indicate an end of the injection. In particular, the radial protrusion 402 can be provided with a specific colour (red for example) to indicate clearly that all the dose of substance 105 is injected.

In this embodiment, the first track portion 301 is shorter than the second track portion 302, as shown FIG. 13. This causes that the needle shield 20A protrudes more out of the external case 50 when it is in the safety position compared to when it is in the initial shielding position. Consequently, a protruding ring 21A provided on the needle shield 20A sticks out of the extremal skirt of external case 50 only when the needle shield 20A is in the safety position (FIG. 5 for example). The user can then see the protruding ring 21A, and clearly notice that the injection device has been used and that the needle shield 20A is in the safety position. In particular, the protruding ring 21A can be provided with a specific colour (red for example) to indicate clearly the safety position.

Figure 15:
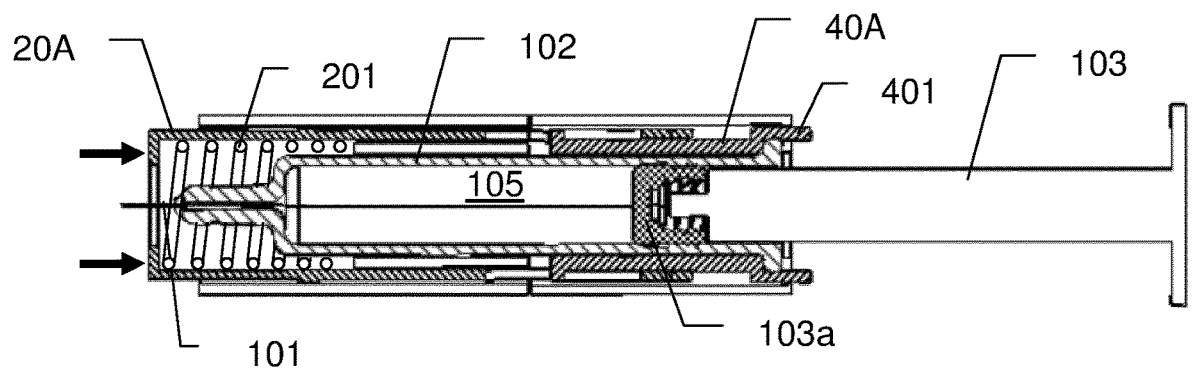
FIG. 15 represents a cross section of the injection device of the first embodiment during pricking, at the beginning of injection.
Figure 16:
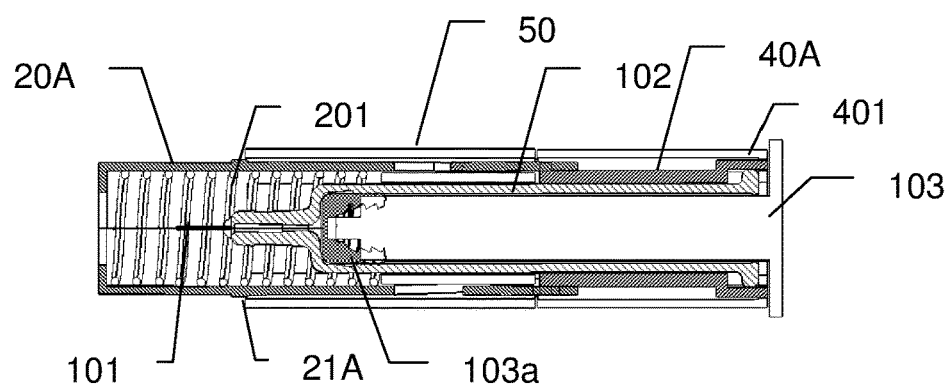
FIG. 16 represents a cross section of the injection device of the first embodiment after injection.

FIGS. 14-16 summarise the different phases of use of the injection device according to the first embodiment.

FIG. 14 shows the injection device before use: substance 105 is in the barrel 102, the protection cap 106 is still attached to the injection device, the plunger rod 103 is in initial position, and the locking actuator 40A is in the non-actuating position, with projection 401 protruding out of the external case 50.

FIG. 15 shows the injection device in a state when pricking occurs: the protection cap 106 has been removed, the needle shield 20A has moved a bit towards the fully retracted position so that the needle 101 is protruding, plunger rod has not moved yet, and the locking actuator 40A is still in the non-actuating position, and locking unit 30A is in the open mode.

FIG. 16 shows the injection device after injection: the plunger rod has reached its final position (fully pushed into the barrel 102, no substance 105 is contained anymore). Consequently, the locking actuator 40A is in the actuating position, so that the locking unit is put in the closed mode and the needle shield 20A, pushed by spring 201, has reached the safety position (protruding ring 21A is outside external case 50), and is locked into this safety position, as explained above.

Figure 17:
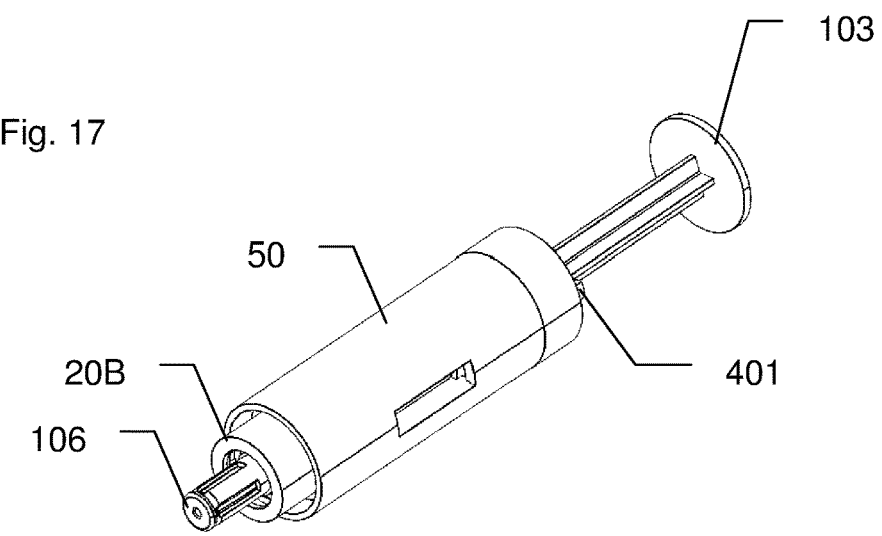
FIG. 17 represents a front perspective view of an injection device according to a second embodiment of the invention, before use.
Figure 18:
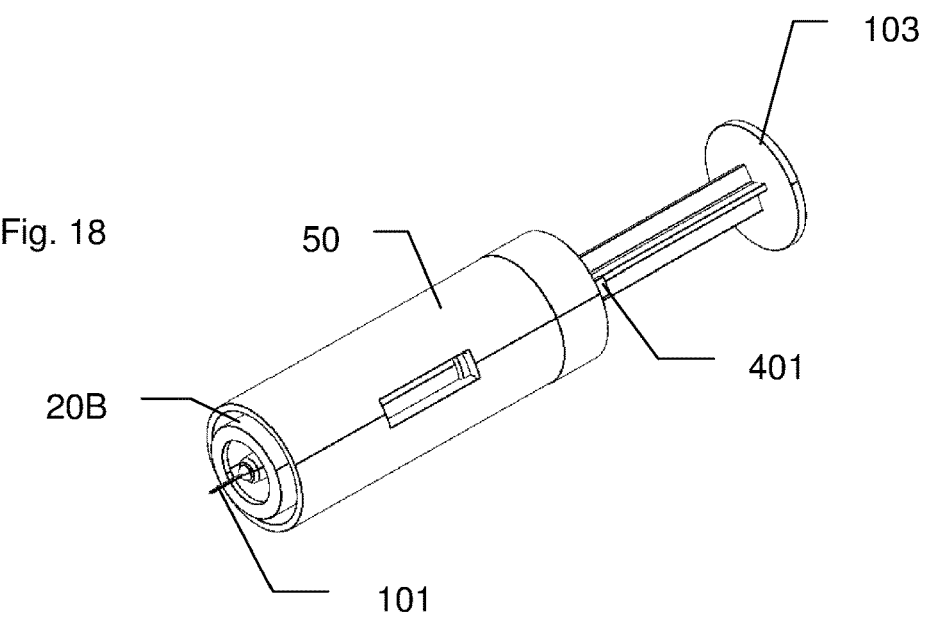
FIG. 18 represents the injection device of FIG. 17 during injection.
Figure 19:
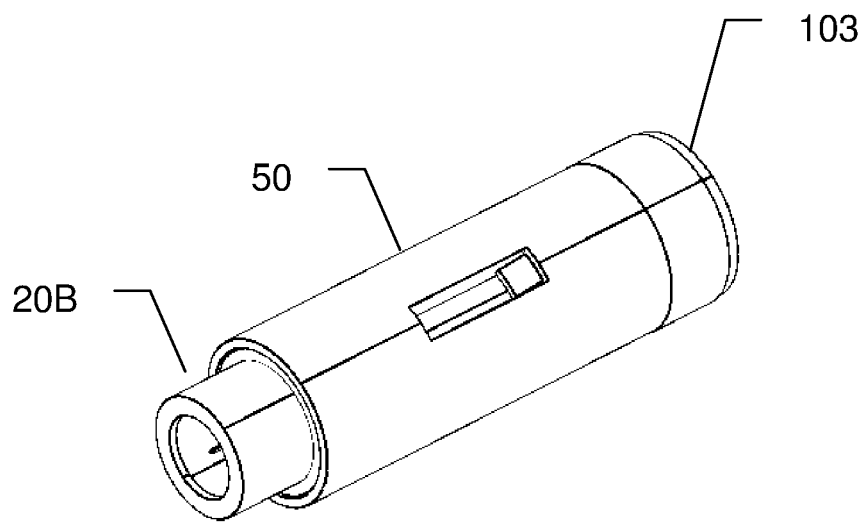
FIG. 19 represents the injection device of FIG. 17 after injection.

FIGS. 17, 18, 19 represent perspective views of an injection device according to a second embodiment of the invention.

Figure 22:
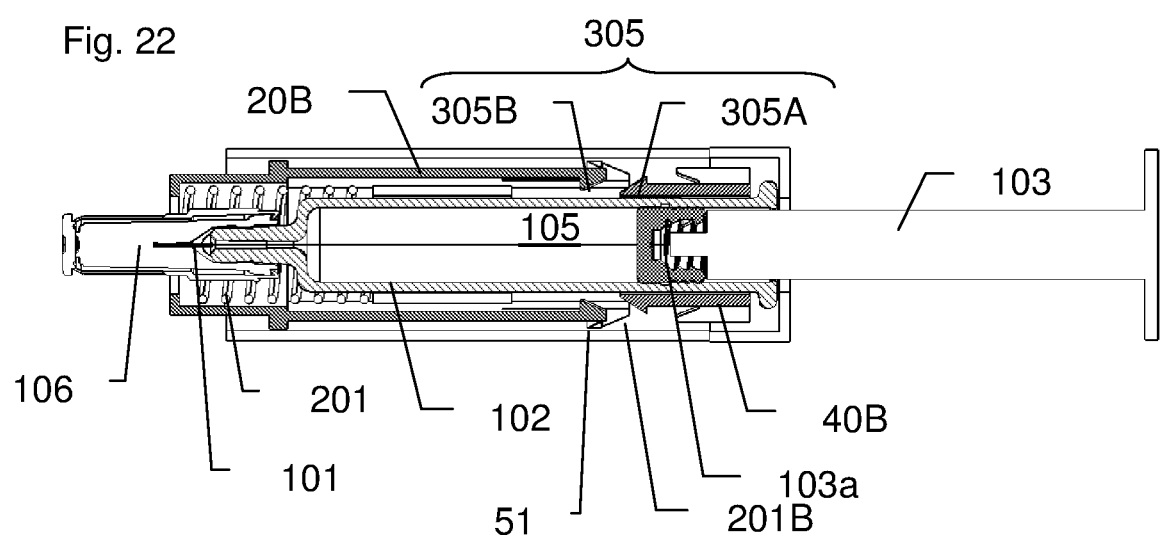
FIG. 22 represents a cross section of the injection device of the second embodiment before use.

In this second embodiment, and as shown FIG. 22, the injection device comprises inside the external case 50:
    a syringe comprising:
        a needle 101 to prick the body,
        a barrel 102 containing a dose of the substance 105 to be injected, and coupled to the external case 50,
        a stopper 103a arranged in sliding engagement inside the barrel 102,
        a plunger rod 103 coupled to the stopper 103a, moveable from an initial position (as shown FIG. 17) to a final position (shown FIG. 19) and to be actuated by a user to inject the dose of the substance 105,
    a needle shield 20B, in an initial shielding position in which the needle shield 20B covers the needle 101,
    a locking actuator 40B
    a spring 201, pushing the needle shield 20B to the left side of FIG. 17, to maintain it into the initial shielding position FIG. 17 represents the injection device before use, with the protective cap 106 covering the needle 101, and plunger rod 103 being in initial position. FIG. 18 represents the injection device during injection, with the protective cap 106 not anymore in attached to the injection device, and the needle shield 20B in the retracted position, so that needle 101 fully sticks out of the needle shield 20B and external case 50. Finally, FIG. 19 represents the injection device after injection, with plunger rod 103 in final position and needle shield 20B in safety position (fully deployed out of external case 50 and covering the needle 101).

Similarly to the first embodiment, an aim of the invention is to provide the capacity to change of pricking site even after a portion of the substance 105 has been injected (requiring the possibility for the needle shield 20B to move forward and backward with a locking unit in a open mode), and to still ensure that after full injection, the needle shield 20B will be secured or locked into the safety position with the locking unit in the closed mode, to avoid unexpected injury or pricking.

Consequently, the injection device of the second embodiment comprises a locking unit 30B (visible for example FIGS. 24-25) with a locking actuator 40B (visible for example FIGS. 21, 20 and 22-26) and the locking unit 30B also comprises a first coupling unit 305 and a second coupling unit 306.

Similarly to the first embodiment, the plunger rod 103 is arranged to push the locking actuator 40B of the second embodiment, when the plunger rod 103 reaches a threshold position, before arriving into the final position. In this aim, the locking actuator 40B comprises projections 401. In the non-actuating position of the locking actuator 40B, the projections 401 are protruding out of the external case 50, so that the end portion of the plunger rod 103 pushes the projections 401 and locking actuator 40B into the actuating position, when the injection is almost complete.

In detail, the first coupling unit 305 is arranged to couple the needle shield 20B with the locking actuator 40B only when the locking actuator 40B is in the actuating position. Elastic legs 305A and 305B are respectively provided onto the locking actuator 40B and onto the needle shield 20B, to allow a snap fit or elastic and irreversible engagement between these parts, when the locking actuator 40B is pushed into the actuating position towards the needle shield 20B being in the retracted position (as the patient is pricked, patient's body pushes the needle shield 20B into the retracted position).

When the locking actuator 40B is coupled to the needle shield 20B, the latter, during removal of the needle 101 out of the patient's body, will pull the locking actuator 40B into the external case 50, to reach the safety position, and a locking position of the locking actuator 40B.

Further, the second coupling unit 306 is arranged to lock the locking actuator 40B in the locking position by coupling the external case 50 with the locking actuator 40B. In the present second embodiment, elastic legs 306A and 306B are respectively provided onto the locking actuator 40B and onto external case 50, to allow a snap fit or elastic and irreversible engagement between these parts. As the barrel 102 is coupled to the external case 50, the locking actuator 40B is indirectly coupled to the barrel 102, when the second coupling unit 306 is coupling the locking actuator 40B to the external case 50.

In practice, after injection, plunger rod 103 has pushed the locking actuator 40B inside the external case 50 in the actuating position. Therefore, the locking unit 30B is in the closed mode, so that the first coupling unit 305 couples the locking actuator 40B to the needle shield 20B (see FIG. 23 before such coupling and FIG. 25 after coupling), and the user, removing the injection device, allows the needle shield 20B (pushed by the spring 201) to deploy out of the external case 50 while pulling together the locking actuator 40B, so that, when the needle shield 20B reaches the safety position, the second coupling unit 306 couples the locking actuator 40B to the external case 50 (see FIG. 24 before such coupling, and FIG. 26 after the coupling).

Figure 20:
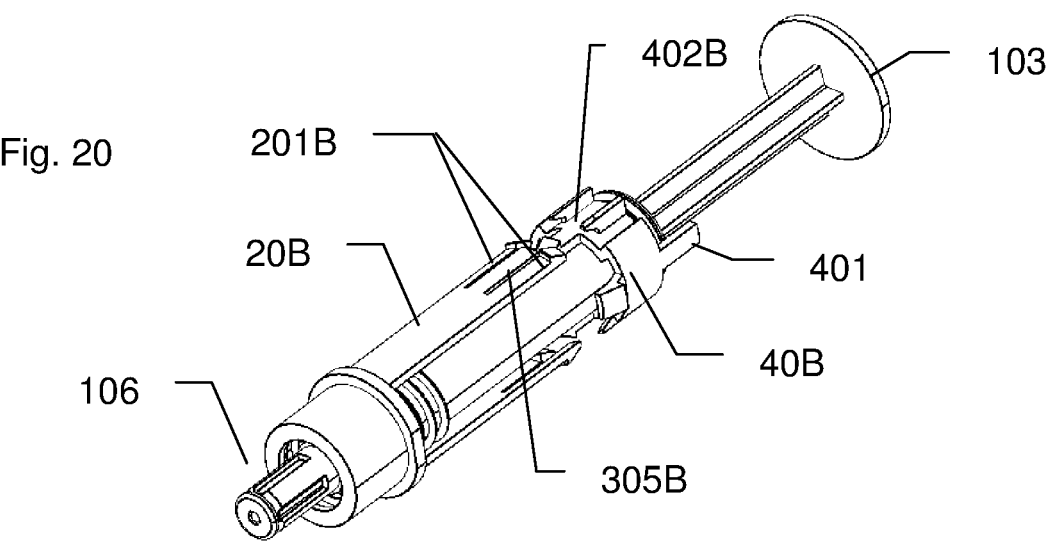
FIG. 20 represents the injection device of FIG. 17 before use, with an external case not shown.
Figure 21:
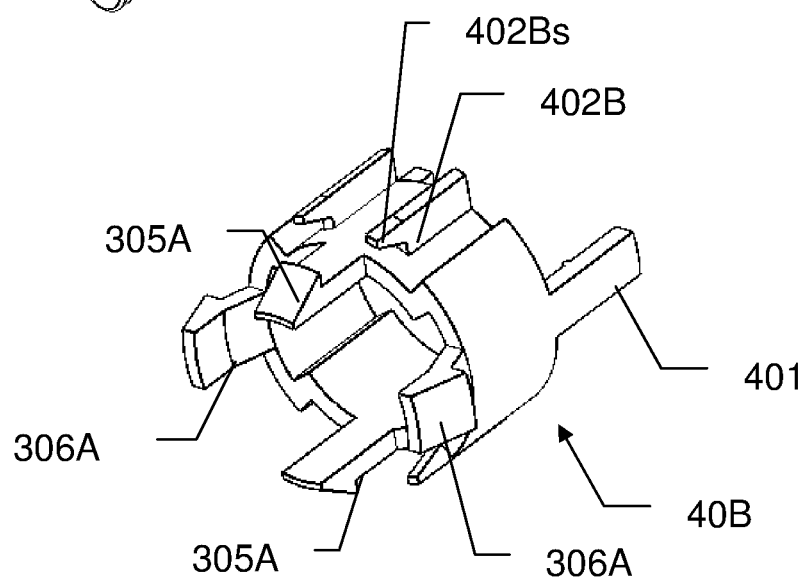
FIG. 21 represents a locking actuator of the injection device according to the second embodiment

Back to FIGS. 20 and 21, one should note that the needle shield 20B is provided with two longitudinal extensions 201B, provided with hook, and arranged on either side of each elastic leg 305B, and that the locking actuator 40B comprises two radial ribs 402B provided on either side of the elastic leg 305A. Then, when the needle shield 20B is coupled to the locking actuator 40B, the longitudinal extensions 201B are in regards of the radial ribs 402B, so that relative axial movements between these parts are not possible.

Then, the needle shield 20B, coupled to the locking actuator 40B, the latter being coupled to the external case 50, cannot move anymore backwards to the retracted position.

Figure 23:
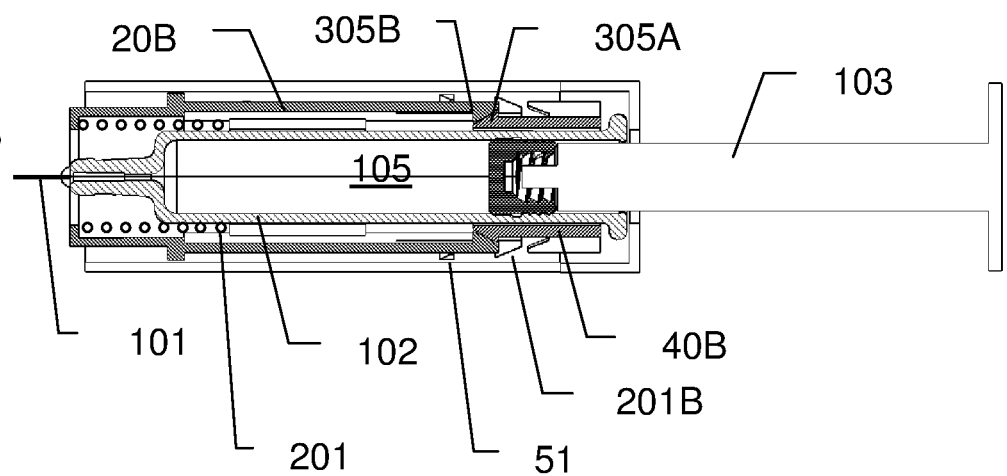
FIG. 23 represents a cross section of the injection device of the second embodiment during injection.

In addition, as visible FIGS. 22 and 23, the hooks of the longitudinal extensions 201B abut on first mechanical stops 51 provided on external case 50 and defining the initial shielding position of the needle shield 20B, to prevent full deployment caused by the spring 201.

As long as the locking actuator 40B is in the non-actuating position, the needle shield 20B can move forward and backward between the initial shielding position (abutting onto the first mechanical stops 51) and the retracted position.

However, and as shown FIG. 21, the radial ribs 402B of the locking actuator 40B are comprising inwardly directed slopes or chamfers 402Bs. Consequently, when the locking actuator 40B is in the actuating position, the inwardly directed slopes or chamfers 402Bs are designed to bend the longitudinal extensions 201B in an inwardly radial direction, so that the hooks of the longitudinal extensions 201B cannot engage the first mechanical stops 51 anymore. As a consequence, the needle shield 20B will not abut onto the first mechanical stops 51, and the needle shield 20B will deploy a bit further out of the external case 50, so as to reach the safety position, where it is locked, by coupling of locking actuator 40B to the external case 50.

The further stroke from the initial shielding position to the safety position is used, similarly to the first embodiment, to uncover a specific (and hidden until now) portion of the needle shield 20B which can be of a specific colour, to indicate that the injection device has been used, and that the needle shield 20B is locked into the safety position.

It is of course understood that obvious improvements and/or modifications for one skilled in the art may be implemented, still being under the scope of the invention as it is defined by the appended claims.

The invention claimed is:

1. An injection device for injecting a substance into a body, comprising:
   a syringe comprising:
      a needle to prick the body,
      a barrel arranged to contain a dose of the substance to be injected,
      a stopper arranged in sliding engagement inside the barrel,
      a plunger rod coupled to the stopper, moveable from an initial position to a final position and to be actuated by a user to inject the dose of the substance,
      a needle shield, arranged to be moveable at least from a retracted position in which the needle can prick the user during injection, to a safety position in which the needle shield covers the needle after injection, and
      a locking unit, arranged to lock the needle shield into the safety position after injection, wherein:
   the locking unit comprises a locking actuator, the locking actuator being moveable with respect to the barrel at least:
      from a non-actuating position, into which the locking unit is in an open mode so that the needle shield can freely move between the retracted position and at least an intermediate position arranged between the retracted position and the safety position, and wherein the needle shield is moveable with respect to the locking actuator,
      to an actuating position, into which the locking actuator is arranged to put the locking unit in a closed mode so that the needle shield can be locked into the safety position, and the locking actuator is moved by the plunger rod from the non-actuating position to the actuating position when the plunger rod reaches a threshold position.

2. The injection device according to claim 1, wherein the locking unit comprises a track and a protrusion arranged to slide in the track and wherein:
   the track is provided on or joined to one of the locking actuator and the needle shield, the protrusion is provided on or joined to the other of the locking actuator and the needle shield,
   the track comprises a first track portion, and a second track portion, and
   the locking actuator is arranged to push the protrusion from the first track portion to the second track portion when the locking actuator moves from the non-actuating position to the actuating position.

3. The injection device according to claim 2, wherein the intermediate position is an initial shielding position in which the needle shield covers at least a tip of the needle, and wherein:
   the first track portion has a first length so that the needle shield can freely move along a first stroke between the initial shielding position to the retracted position, and
   the second track portion has a second length, the second length being greater than the first length, so that the safety position is separated from the initial shielding position by an additional stroke of the needle shield.

4. The injection device according to claim 2, wherein the locking unit comprises a flexible leg having a free end arranged between the first track portion and the second track portion, and wherein the flexible leg is flexed by the protrusion passing from the first track portion to the second track portion.

5. The injection device according to claim 4, wherein the free end of the flexible leg is a backstop preventing the protrusion from going back to the first track portion, after the protrusion has been pushed into the second track portion.

6. The injection device according to claim 1, wherein:
the locking unit comprises a first coupling unit arranged to couple the needle shield with the locking actuator only when the locking actuator is in the actuating position,
the locking actuator coupled with the needle shield is moveable from the actuating position to a locking position, and
the locking unit comprises a second coupling unit arranged to lock the locking actuator in the locking position.

7. The injection device according to claim 6, wherein the first coupling unit and/or the second coupling unit is a snap fit unit comprising:
a male portion,
a female portion, and
an elastic portion arranged to deflect during coupling to allow engagement of the male portion with the female portion, and to maintain engagement of the male portion with the female portion after coupling.

8. The injection device according to claim 6, wherein the intermediate position is an initial shielding position into which the needle shield covers at least a tip of the needle, the injection device comprising a first mechanical stop defining the initial shielding position, so that the needle shield can freely move along a free stroke between the initial shielding position to the retracted position, wherein when the needle shield is coupled with the locking actuator, the first coupling unit and or the locking actuator allow the needle shield to pass over the first mechanical stop, so that the safety position is separated from the initial shielding position by an additional stroke of the needle shield.

9. The injection device according to claim 1, comprising elastic means arranged to push the needle shield into the safety position.

10. The injection device according to claim 1, comprising:
an end of injection indicator embarked on the locking actuator, and
a window, arranged:
to hide from the user the end of injection indicator when the locking actuator is in the non-actuating position, and
to render visible to the user the end of injection indicator when the locking actuator is in the actuating position.

11. The injection device according to claim 1, comprising:
a safety indicator embarked on the needle shield, and
a skirt, arranged:
to hide from the user the safety indicator when the needle shield is not in the safety position, and
to render visible to the user the safety indicator when the needle shield is in the safety position.

12. The injection device according to claim 1, wherein the threshold position is located in a range of 70%-100% of a stroke of the plunger rod from the initial position to the final position.

13. The injection device according to claim 1, wherein the locking actuator comprises a projection arranged to protrude out of an external surface of the injection device, and is arranged to be pushed by the plunger rod when the plunger rod moves the locking actuator from the non-actuating position to the actuating position.

14. The injection device according to claim 1, comprising a needle cap to be detached from the syringe by the user before use.

15. The injection device according to claim 1, comprising the dose of the substance to be injected.

* * * * *